US00PP31367P2

(12) United States Plant Patent
Probst

(10) Patent No.: US PP31,367 P2
(45) Date of Patent: Jan. 14, 2020

(54) ***COREOPSIS* PLANT NAMED 'ICE WINE'**

(50) Latin Name: ***Coreopsis* hybrid**
Varietal Denomination: Ice Wine

(71) Applicant: Darrell R. Probst, Hubbardston, MA (US)

(72) Inventor: Darrell R. Probst, Hubbardston, MA (US)

( * ) Notice: Subject to any disclaimer, the term of this patent is extended or adjusted under 35 U.S.C. 154(b) by 0 days.

(21) Appl. No.: 15/998,095

(22) Filed: Jun. 29, 2018

(51) Int. Cl.
*A01H 5/02* (2018.01)
*A01H 6/14* (2018.01)

(52) U.S. Cl.
USPC ..... Plt./417

(58) Field of Classification Search
USPC ..... Plt./417
CPC . A01H 5/02; A01H 5/00; A01H 5/025; A01H 6/14
See application file for complete search history.

(56) References Cited

U.S. PATENT DOCUMENTS

PP23,035 P2 * 9/2012 Probst ..... A01H 6/14 Plt./417
PP27,414 P2 * 11/2016 Probst ..... A01H 6/14 Plt./417

OTHER PUBLICATIONS

Art Form Nurseries *Coreopsis* Satin and Lace Ice Wine 2017, retrieved on Apr. 24, 2019, retrieved from the Internet at https://www.artformnurseries.com/ws-perennials/coreopsis-ice-wine, 2 pp. (Year: 2017).*

Emerald Coast Growers Starter Plants 2017-2018, retrieved on Apr. 24, 2019, retrieved from the Internet at http://www.ecgrowers.com/v/vspfiles/brochures/ecg_catalog_2017-18_lowrez.pdf, cover page, pp. 1,3,21,108-110,112-113. (Year: 2018).*

* cited by examiner

*Primary Examiner* — June Hwu
(74) *Attorney, Agent, or Firm* — Penny J. Aguirre

(57) ABSTRACT

A new cultivar of hybrid *Coreopsis* named 'Ice Wine' that is characterized by its sturdy, well-branched plant habit reaching an average of 45 cm in height and 75 cm in width, its floriferous and long blooming season of nearly sterile inflorescences that do not require deadheading; bloom commences in early July and lasts until frost in Kensington, Conn., its medium sized inflorescences with ray florets that are bright white in color with a distinct eyezone that is maroon in color, its resistance to powdery mildew and leafspot and its cold hardiness at least to U.S.D.A. Zone 5a.

2 Drawing Sheets

Botanical classification: *Coreopsis* hybrid.
Variety denomination: 'Ice Wine'.

CROSS REFERENCE TO A RELATED APPLICATION

This application is related to U.S. Plant Patent for a plant derived from the same breeding program that is entitled *Coreopsis* Plant Named 'Berry Chiffon' (U.S. Plant Pat. No. 27,414) and *Coreopsis* Plant Named 'Star Cluster' (U.S. Plant Pat. No. 23,035).

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosure and/or sales prior to the filing date but less than one year prior to the effective filing date. Publications include but are not limited to listings on websites by Hirt's Gardens, Romence Gardens, Emerald Coast Growers, Faddegon's Nursery, Santa Rosa Gardens, and Sugar Creek Gardens Plant Nursery.

BACKGROUND OF THE INVENTION

The present invention relates to a new and distinct cultivar of *Coreopsis* plant, botanically of hybrid origin and known as *Coreopsis* 'Ice Wine' and will be referred to hereinafter by its cultivar name, 'Ice Wine'. The new cultivar of *Coreopsis* is an herbaceous perennial grown for landscape and container use.

The new Invention arose from an ongoing controlled breeding program in New Braintree, Mass. The objective of the breeding program is to develop hybrid cultivars of *Coreopsis* with unique and superior garden attributes. In particular, to develop cultivars that are long-lived, sturdy, exhibit a true perennial habit and cold hardy to at least U.S.D.A. Zone 5 in a wide range of flower colors and plant forms that do not require vernalization to initiate flowering.

The Inventor made a controlled cross in August of 2013 in New Braintree, Mass. between an unnamed and unpatented proprietary plant from his breeding program as the female parent and pollen that was pooled from a variety of unnamed and unpatented proprietary plants from his breeding program as the male parent. The exact characteristics of the pollen parent are therefore unknown. 'Ice Wine' was selected in September of 2014 as a single unique plant amongst the resulting seedlings.

Asexual propagation of the new cultivar was first accomplished by stem cuttings under the direction of the Inventor in Kensington, Conn. in September of 2014. Asexual propagation by stem cuttings has shown that the characteristics of the new cultivar are stable and are reproduced true to type in successive generations.

SUMMARY OF THE INVENTION

The following traits have been repeatedly observed and are determined to be the characteristics of the new cultivar. These attributes in combination distinguish 'Ice Wine' as a unique cultivar of *Coreopsis*.

1. 'Ice Wine' exhibits a sturdy, well-branched plant habit reaching an average of 45 cm in height and 75 cm in width.
2. 'Ice Wine' exhibits a floriferous and long blooming season of nearly sterile inflorescences that do not require deadheading; bloom commences in early July and lasts until frost in Kensington, Conn.
3. 'Ice Wine' exhibits medium sized inflorescences with ray florets that are bright white in color with a distinct, non-flushing eyezone that is maroon in color.
4. 'Ice Wine' exhibits resistance to powdery mildew (*Podosphaera macularis*) and leafspot (*Pseudomonas cichorii*).
5. 'Ice Wine' exhibits cold hardiness at least to U.S.D.A. Zone 5a.

The female parent of 'Ice Wine' differs from 'Ice Wine' in having inflorescences with ray florets that are yellow in color and in having a taller plant height and a floppy plant habit. 'Ice Wine' can be most closely compared to *Coreopsis* cultivars 'Berry Chiffon' and 'Star Cluster'. 'Berry Chiffon' is similar to 'Ice Wine' in being from a closely related breeding line to 'Ice Wine' in having thread-leaf type foliage and in having a similar inflorescence color and cold hardiness. 'Berry Chiffon' differs from 'Ice Wine' in having inflorescences with ray florets that are solid creamy white in color with eye zone color flushing into the ray florets. 'Star Cluster' is similar to 'Ice Wine' in having inflorescences that are similar in color. 'Star Cluster' differs from 'Ice Wine' in having wider, non-thread like leaf foliage and inflorescences with ray florets that have a very small, non-distinct purple eye zone.

BRIEF DESCRIPTION OF THE DRAWINGS

The accompanying colored photographs illustrate the overall appearance and distinct characteristics of the new *Coreopsis*. The photographs were taken of a 2-year-old plant of 'Ice Wine' as grown outdoors in a 3-gallon container in Kensington, Conn.

The photograph in FIG. 1 provides a side view of 'Ice Wine' and shows the plant habit in bloom.

Figure 1:
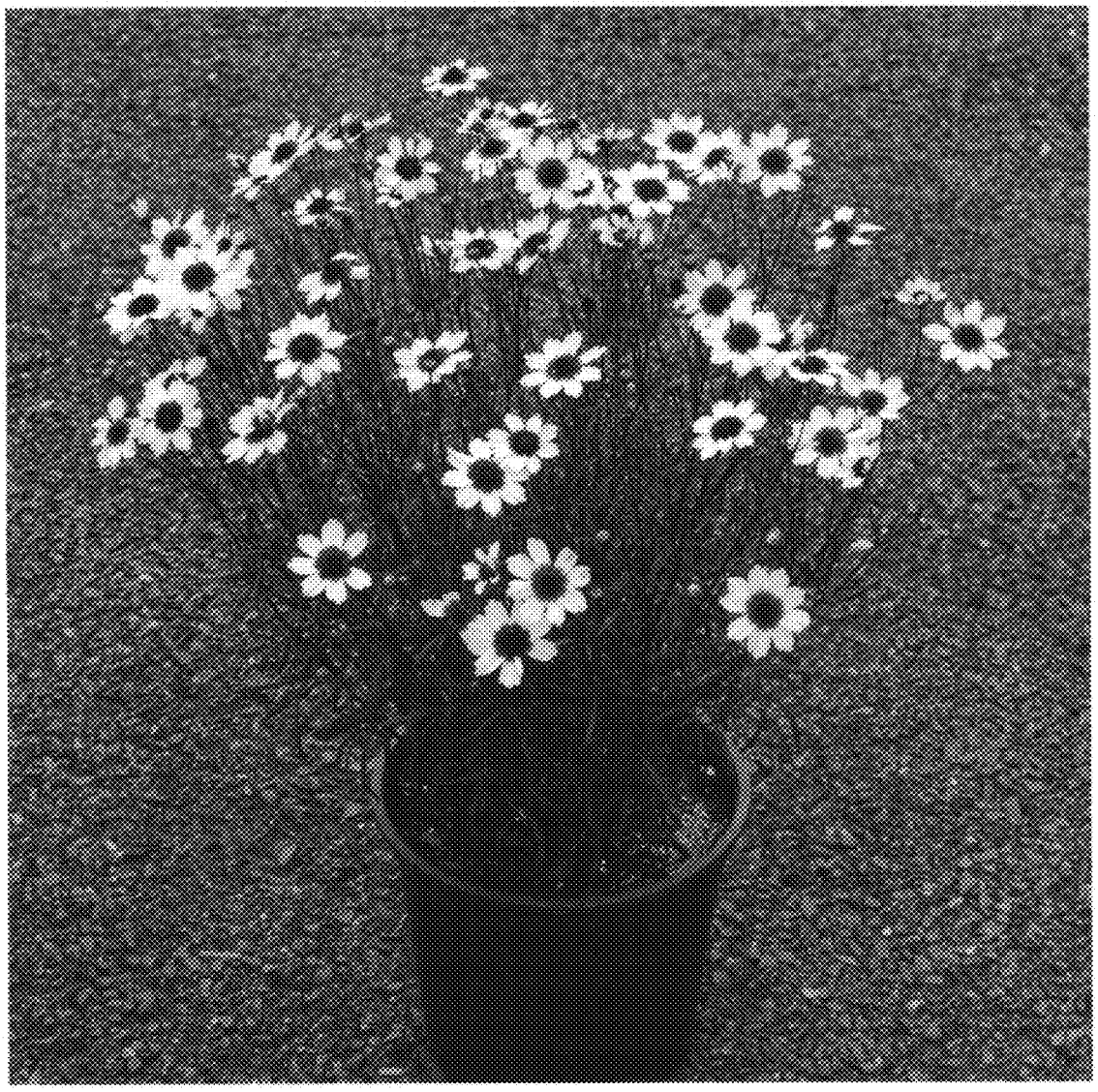
Figure 2:
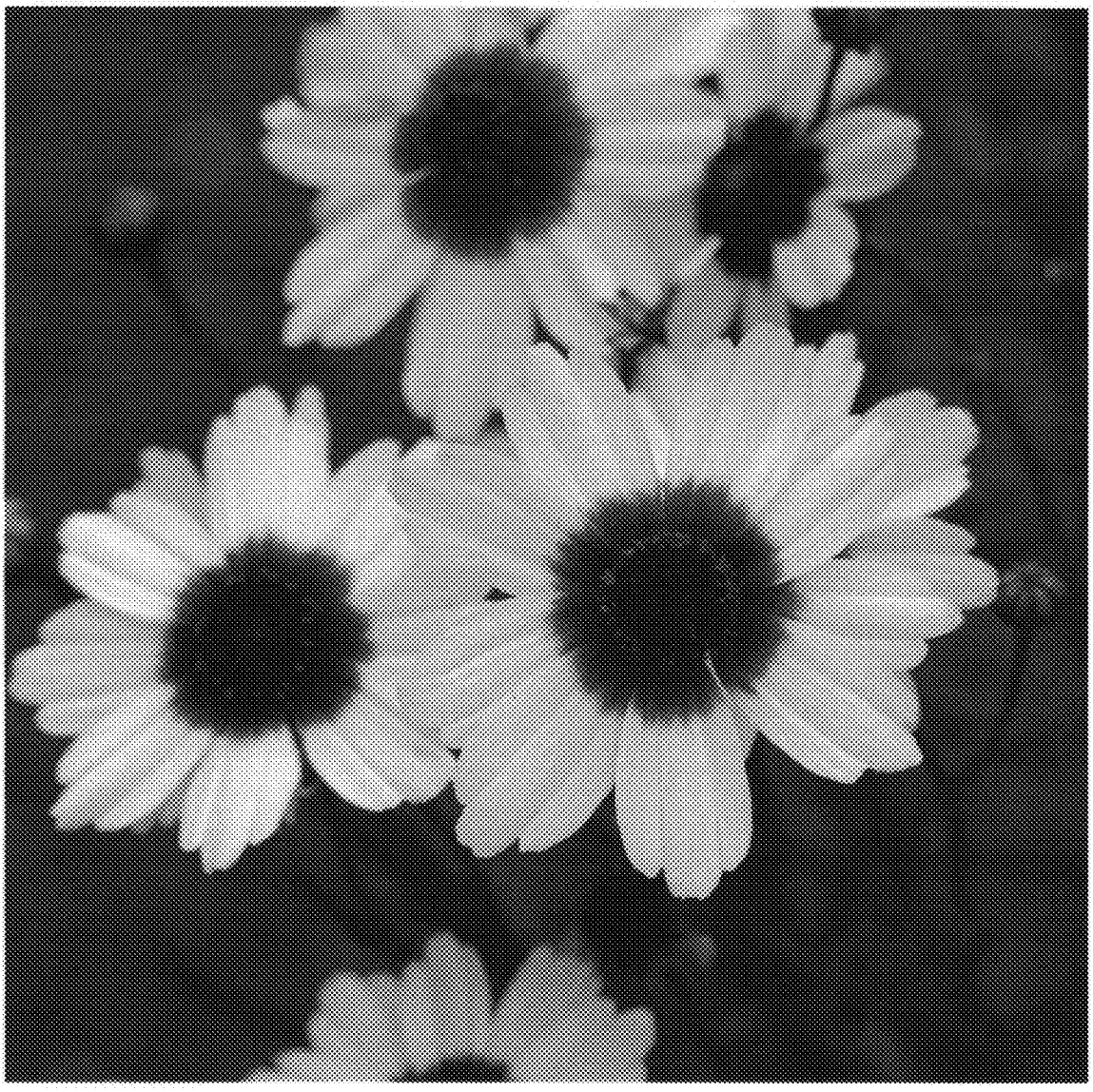

The photograph in FIG. 2 provides a close-up view of the inflorescences of 'Ice Wine'.

The colors in the photographs are as close as possible with the photographic and printing technology utilized and the color values cited in the detailed botanical description accurately describe the colors of the new *Coreopsis*.

DETAILED BOTANICAL DESCRIPTION

The following is a detailed description of 3-month-old plants of 'Ice Wine' as grown outdoors in a one-gallon container in Kensington, Conn. The phenotype of the new cultivar may vary with variations in environmental, climatic, and cultural conditions, as it has not been tested under all possible environmental conditions. The color determination is in accordance with The 2015 R.H.S. Colour Chart of The Royal Horticultural Society, London, England, except where general color terms of ordinary dictionary significance are used.

General description:

*Blooming period*.—Blooms from early July until frost in Kensington, Conn.

*Plant type*.—Herbaceous perennial.

*Plant habit*.—Clump-forming, compact, upright leafy flowering stems with inflorescences held above the foliage.

*Height and spread*.—An average of 45 cm in height and 75 cm in width in the lanscape.

*Cold hardiness*.—At least to U.S.D.A Zone 5a.

*Diseases and pests*.—Resistance to powdery mildew (*Podosphaera macularis*) and leafspot (*Pseudomonas cichorii*), no susceptibility or resistance to pests has been observed.

*Root description*.—Fibrous and fine, NN155A in color.

*Propagation*.—Stem cuttings.

*Time required for root initiation*.—An average of 10 days for root initiation.

*Growth rate*.—Moderately vigorous.

Stem description:

*Shape*.—Rounded to tetragonal, solid.

*Stem color*.—146A.

*Stem strength*.—Strong.

*Stem size*.—Main stems; an average of 28 cm in length and 4 mm in width, lateral stems; an average of 15 cm in length (excluding peduncles) and 2 mm in width.

*Stem surface*.—Glabrous, smooth, and dull.

*Branching habit*.—Freely branched, an average of 10 basal main stems, lateral stems typically branched as oppositely arranged pairs at each node, up to 6 lateral stems (3 pairs) per main stem.

*Internode length*.—An average of 2 cm.

Foliage description:

*Leaf division*.—Simple.

*Leaf margins*.—Entire.

*Leaf size*.—Entire leaves; an average of 7.5 cm in length and 7 cm in width, ranges from 3 to 4 to 5 leaves; center lobe an average of 5 cm in length and 4 mm in width, lateral lobes an average of 4 cm in length and in 4 mm width.

*Leaf shape*.—Narrow obanceolate.

*Leaf base*.—Cuneate.

*Leaf apex*.—Bluntly acute.

*Leaf venation*.—Pinnate, inconspicuous, same color as leaf.

*Leaf attachment*.—Sessile.

*Leaf arrangement*.—Opposite.

*Leaf surface*.—Upper and lower surfaces; smooth, dull, and glaucous.

*Leaf color*.—Young and mature upper and lower surface; 137A.

Flower description:

*Inflorescence type*.—Composite with a single row of ray florets surrounding disk florets in the center, inflorescences are borne on branch terminals in loose corymbs.

*Lastingness of inflorescence*.—8 to 10 days until senescence of ray flowers, Phyllaries and disk flowers are persistent.

*Fragrance*.—Citrus scent, pleasant.

*Quantity of inflorescences*.—Free flowering, an average of 5 corymbs per main branch, an average of 3 composites per corymb.

*Inflorescence size*.—Corymbs; an average of 12 cm in length and 6 cm in width, composite; an average of 2 cm in depth and 5 cm in diameter with disk portion up to 1 cm in diameter.

*Inflorescence buds*.—Flattened globose in shape, an average of 6 mm in depth and 8 mm in diameter, smooth and shiny surface; color; a blend of 21A and 20A, suffused at the base with 146A, streaks of 183A and 200A held at the margins.

*Peduncle*.—Rounded in shape, strong, an average of 7 cm in length and 1 mm in diameter, 146A in color, smooth and glabrous surface.

Phyllaries (involucral bracts):

*Phyllary number*.—2 rows; outer (lower) row 10, inner (upper) row 9.

*Phyllary arrangement*.—Outer (lower) phyllaries; unfused, held upwards with the apex and recurved downwards, inner (upper) phyllaries; overlap and surround receptacle with apical portion reflexed (campanulate-like).

*Phyllary size*.—Outer (lower) phyllaries; an average of 3 mm in length and 1 mm in width, inner (upper) phyllaries; an average of 8 mm in length and 4 mm in width.

*Phyllary color*.—Upper and lower surfaces, outer (lower) phyllaries; 139B, margins 142B, inner (upper) phyllaries; transluscent, a blend of 168A and 165B, margins flushed with 183A, base 146A.

*Phyllary texture*.—Outer (lower) phyllaries; glabrous and smooth on both surfaces, inner (upper) phyllaries; glabrous and slightly waxy on both surfaces.

*Phyllary apex*.—Acute.

*Phyllary base*.—Truncate.

*Phyllary shape*.—Outer (lower) phyllaries; lanceolate, inner (upper) phyllaries; lanceolate.

Ray florets (sterile):

*Number*.—Ranging between 9 and 11.

*Shape*.—Oblanceolate, with the appearance of 3 longitudinal sections.

*Size*.—An average of 2 cm in length and 1.5 cm in width.

*Apex*.—Rounded with three rounded lobes.

*Base*.—Cuneate.

*Margins*.—Entire on sides with lobed and notched apex.

*Aspect*.—Held mainly horizontal and slightly upwards, perpendicular to peduncle, some florets are slightly overlapping.

*Texture*.—Both surfaces; glabrous, dull, and satiny.

*Color*.—Upper and lower surfaces when opening; a blend of 9D and 155A, eye zone (average of 2.8 mm in length) a blend of 71A and 61A and N34A, upper surface when fully open; 155A, eye zone (average of 4 mm in length) a blend of 71A and 61A and N34A with very base N34A, lower surface fully open; 157A with lower portion lightly suffused with 72B.

Disk florets (male and female):

*Number*.—An average of 120.

*Shape*.—Tubular, corolla is fused, flared at apex.

*Size*.—Average of 7 mm in length and 0.75 mm in width.

*Color*.—En masse; 171A, corolla; (tube) transluscent, 20A, flared portion 183A.

*Receptacle*.—An average of 7 mm in diameter and 2 mm in depth, 139B in color.

Reproductive organs:

*Presence*.—Disk flowers only.

*Gynoecium*.—1 Pistil; an average of 6 mm in length, style; very fine and 161A in color, bifid pillose, stigma; 172A in color with recurved branches about 0.5 mm in length, ovary is inferior, oblong in shape, an average of 2 mm in length and 1 mm in width, and 1A in color.

*Androecium*.—4 stamens, fused into tube surrounding style, an average of 3 mm in length and less than 0.5 mm in width, 202A in color, pollen was not present.

*Seed*.—Seed development has been observed to be very minimal; nearly sterile, plants available for data collection did not set seed.

It is claimed:

1. A new and distinct cultivar of *Coreopsis* plant named 'Ice Wine' as herein illustrated and described.

* * * * *